US00PP35711P2

(12) United States Plant Patent
Clark

(10) Patent No.: US PP35,711 P2
(45) Date of Patent: Mar. 26, 2024

(54) ***Coleus* PLANT NAMED 'UF21-83-1'**

(50) Latin Name: *Coleus scutellarioides*
Varietal Denomination: UF21-83-1

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/445,286

(22) Filed: Jun. 20, 2023

(51) Int. Cl.
*A01H 5/12* (2018.01)
*A01H 6/00* (2018.01)

(52) U.S. Cl.
USPC ..... Plt./469
CPC ..... *A01H 6/00* (2018.05)

(58) Field of Classification Search
USPC ..... Plt./469
CPC ..... A01H 5/12
See application file for complete search history.

(56) References Cited

U.S. PATENT DOCUMENTS

PP34,066 P2 3/2022 Clark

*Primary Examiner* — Kent L Bell
(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF21-83-1' having a combination of desirable traits that make it well-suited for use as an annual plant in the summer landscape. 'UF21-83-1' has consistent foliage color patterning, and fast growth rate and vigor in the greenhouse and landscape. 'UF21-83-1' has ruffled, highly lobed foliage that is predominantly dark red with consistent yellowish green leaf margins and a yellowish green base on the upper surface and undersides. 'UF21-83-1' maintains these contrasting colors and patterns in both sun and shade. 'UF21-83-1' is upright in habit, but it is highly branched and spreading in form, growing wider than it does tall.

3 Drawing Sheets

Genus and species: *Coleus scutellarioides*.
Cultivar denomination: 'UF21-83-1'.

BACKGROUND OF THE NEW CULTIVAR

The invention relates to a new and distinct cultivar of *Coleus* plant named 'UF21-83-1'. The new cultivar 'UF21-83-1' originated from an open pollination conducted in May-November 2020 in Citra, Florida between the female *Coleus* plant 'UF20-88-1' (unpatented) and an unknown male *Coleus* plant. A single seedling was chosen in May 2021 for further asexual propagation in Gainesville, Florida.

The new cultivar 'UF21-83-1' has been reproduced asexually for over 18 months through vegetative meristem tip cuttings and has been found to retain its distinctive characteristics through successive asexual propagations. 'UF21-83-1' was first propagated asexually by vegetative meristem tip cuttings in May 2021 in Gainesville, Florida, and has remained true-to-type since that time.

Plant Breeder's Rights for the new cultivar 'UF21-83-1' have not been applied for, and 'UF21-83-1' has not been made publicly available more than one year prior to the filing date of this application.

SUMMARY OF THE INVENTION

The new cultivar 'UF21-83-1' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'UF21-83-1' was selected for its unique, ruffled, and highly lobed-shape leaves with consistent color, and because it has not been observed to produce flowers in any field or greenhouse trials. It performs well in any garden location and has excellent vigor. 'UF21-83-1' maintains consistent dark red leaf coloration with yellowish green leaf margins in both sun and shade.

The following are the most outstanding and distinguishing characteristics of 'UF21-83-1' when grown under normal horticultural practices in Gainesville, Florida: (1) 'UF21-83-1' has the combination of vigorous, upright habit and spreading growth form, and excellent heat tolerance; (2) 'UF21-83-1' has ruffled, highly lobed foliage that is predominantly dark red with consistent yellowish green leaf margins and a yellowish green base on the upper surface and undersides that is significantly different than other *Coleus* plants known to the Inventor; (3) it has stability in foliage color in both sun and shade conditions, and it has a vigorous growth habit with excellent lateral branching, making it suitable for propagators and producers; and (4) 'UF21-83-1' has been observed to have long-season performance in landscape trials in Gainesville, Florida.

When 'UF21-83-1' is compared to the female parent 'UF20-88-1', both plants have large, highly lobed leaves with ruffled edges that are slightly longer than they are wide. However, 'UF21-83-1' leaves are dark red, with well-defined yellowish green margins and a yellowish green base on the upper surface and leaf undersides. In contrast, 'UF20-88-1' has leaves that are colored burgundy red with chartreuse margins and leaf undersides. 'UF21-83-1' has a vigorous upright growth habit with a spreading form that is well-branched, whereas 'UF20-88-1' has a more compact growth habit, with equivalent lateral branching but a less spreading form.

DESCRIPTION OF THE FIGURES

This new *Coleus* cultivar 'UF21-83-1' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar; and FIG. 3 shows a close-up view of the foliage of the new *Coleus* cultivar.

DETAILED BOTANICAL DESCRIPTION OF THE CULTIVAR

Figure 1:
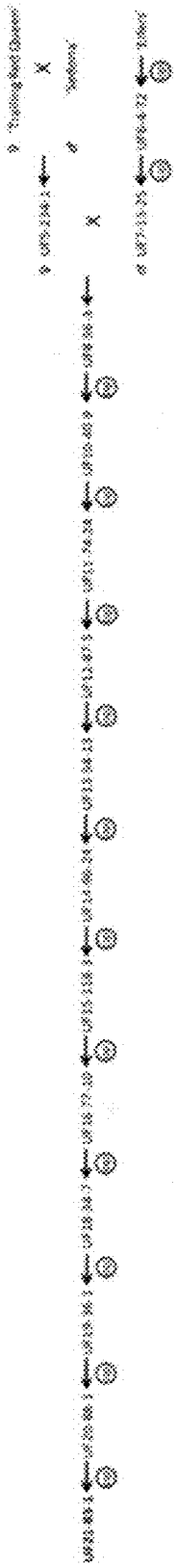
FIG. 1 shows the pedigree of the new *Coleus* cultivar 'UF21-83-1' as is shown and described herein.
Figure 2:
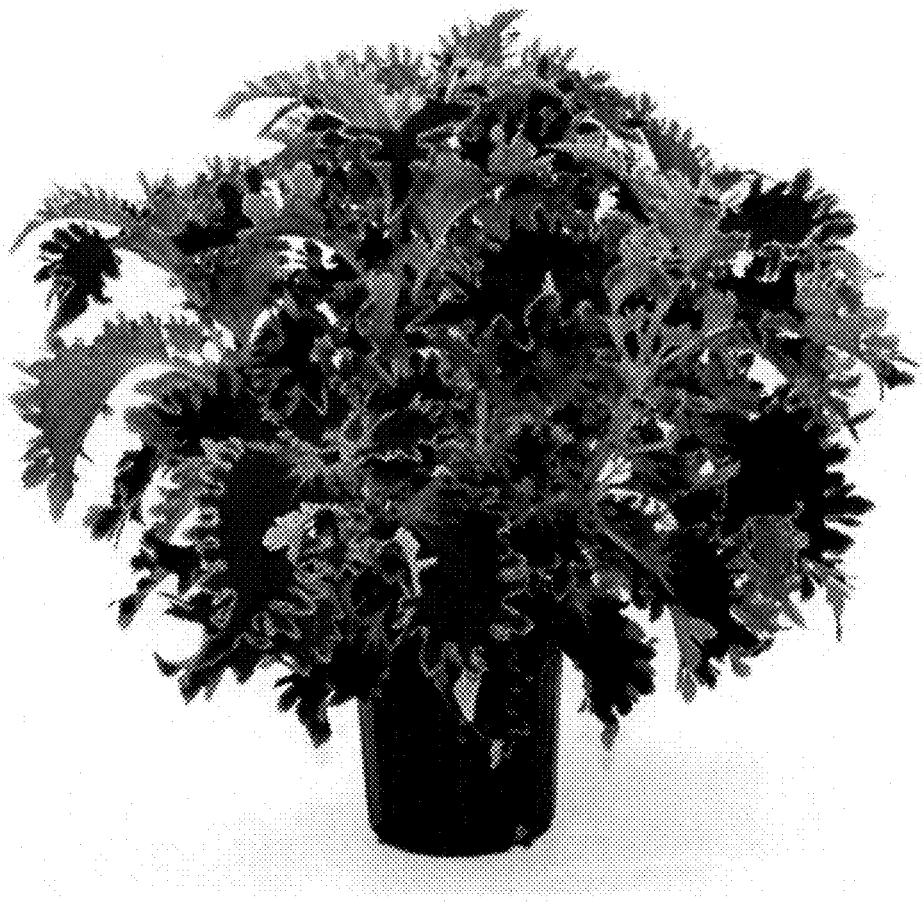
FIGS. 2 and 3 were taken from plants grown eleven weeks from unrooted cuttings in September-December 2022 in a glass-covered greenhouse in Gainesville, Florida.
Figure 3:
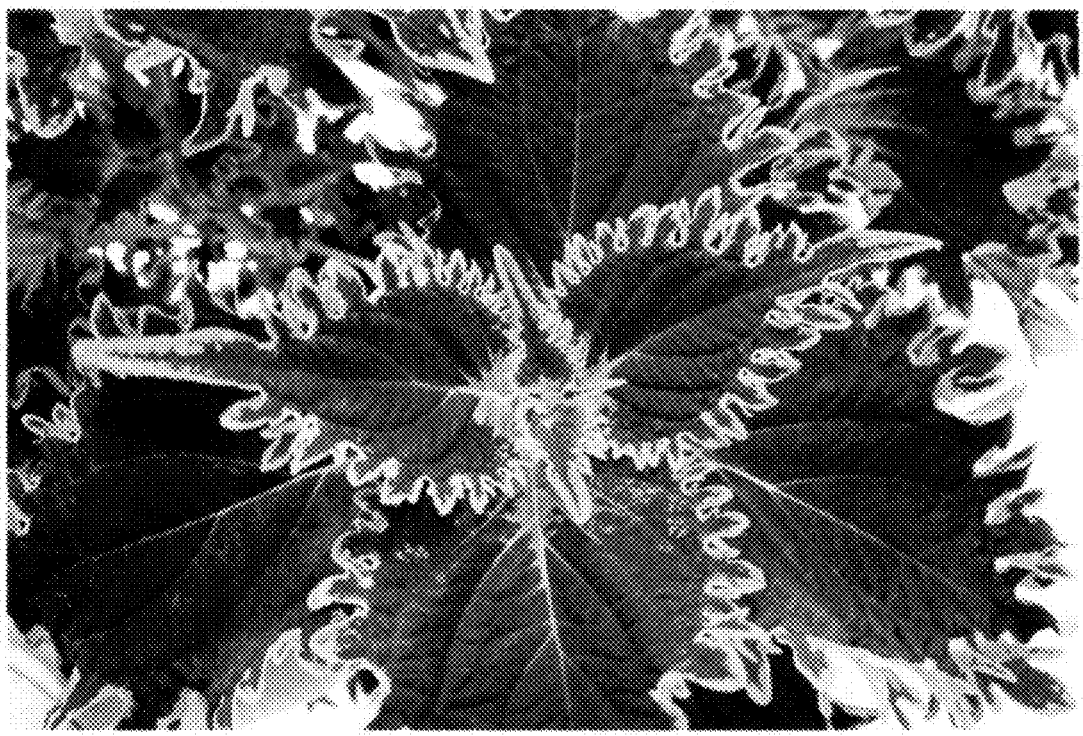

Foliage color was determined under full sun conditions in the middle of the day in a glass-covered greenhouse. Color references are to the RHS Colour Chart of The Royal Horticultural Society of London (RHS), 2007 5th Edition. *Coleus* leaves are rarely one solid color but encompass hues, shades and tints, and color patterns differ from one genotype to another due to varying levels of variegation. The following detailed description of 'UF21-83-1' was obtained using eleven-week-old plants grown from unrooted cuttings in September-December 2022 in a glass-covered greenhouse in Gainesville, Florida. The plants were propagated in mist for ten days after cuttings were stuck, pinched, then grown in one-gallon pots for approximately nine and a half additional weeks.

Botanical Description

Botanical classification:
- *Family.*—Lamiaceae.
- *Botanical name.*—*Coleus scutellarioides.*
- *Common name.*—*Coleus.*
- *Cultivar name.*—'UF21-83-1'.

Parentage:
- *Female or seed parent.*—'UF20-88-1'.
- *Male or pollen parent.*—Unknown.

Plant description:
- *Form.*—Spreading.
- *Habit.*—Upright.
- *Height* (*from top of soil*).—40-45 cm.
- *Width* (*horizontal plant diameter*).—60-65 cm.

Propagation:
- *Type cuttings.*—Vegetative meristems having at least 1 node.
- *Time to initiate roots.*—3-4 days.
- *Time to produce a rooted cutting.*—7-10 days.
- *Root habit.*—Fibrous.
- *Root description.*—Callus forms in 2-3 days, roots initiate in 3-4 days and become a highly branched cutting in 7-10 days.

Branches:
- *Quantity per plant.*—Approximately 9.
- *Branch color.*—RHS 143B (yellow green).
- *Texture.*—Smooth.
- *Pubescence.*—Not present.
- *Stem description.*—Square-shaped stem.
- *Branch diameter.*—0.8-0.9 cm at the base of a 35-cm-long branch.
- *Branch length.*—35-40 cm.
- *Internode length.*—Approximately 4.5 cm measured at mid-branch.
- *Anthocyanin.*—Not present.

Leaves:
- *Quantity of leaves per branch.*—18-20.
- *Arrangement.*—Opposite.
- *Fragrance.*—Not fragrant.
- *Shape.*—Ovate.
- *Length.*—14-15 cm.
- *Width.*—11-12 cm.
- *Apex.*—Broadly acute.
- *Base.*—Attenuate.
- *Margin.*—Highly lobed.
- *Leaf texture.*—Adaxial (top): Pulverulent. Abaxial (bottom): Smooth.
- *Venation color.*—Upper surface: Apex: RHS 187A (dark red). Base: RHS 142C (yellow green). Lower surface: RHS 142C (yellow green).
- *Venation pattern* (*both upper and lower surfaces*).—Reticulate.
- *Color, immature leaf.*—Upper surface: Major color: RHS 187A (dark red). Margins: RHS 134A (yellowish green). Base: RHS 134A (yellowish green). Lower surface: Major color: RHS 135C (yellowish green). Around veins: RHS 187A (dark red).
- *Color, mature leaf.*—Upper surface: Major color: RHS 187A (dark red). Margins: RHS 134A (yellowish green). Base: RHS 134A (yellowish green). Lower surface: Major color: RHS 135C (yellowish green). Around veins: RHS 187A (dark red).
- *Petiole length.*—4.5 cm.
- *Petiole diameter.*—0.3-0.4 cm.
- *Petiole color.*—RHS 143B (yellow green).
- *Petiole texture.*—Smooth, no pubescence.

Flowers and seeds: Flowers and seeds have not been observed during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

Comparison with known cultivars: When compared to the *Coleus* cultivar 'UF18-62-10' (U.S. Plant Pat. No. 34,066, commercial name Vulcan), the new *Coleus* cultivar 'UF21-83-1' has a leaf coloration of dark red with yellowish green margins and a yellowish green base on the upper surface of mature leaves, whereas 'UF18-62-10' has a leaf coloration of dark red with a center coloration of purplish red and light green margins on the upper surface of mature leaves.

What is claimed is:

1. A new and distinct *Coleus scutellarioides* plant named 'UF21-83-1' as shown and described herein.

* * * * *